United States Patent [19]
Garcia-Sastre et al.

[11] Patent Number: 6,146,642
[45] Date of Patent: Nov. 14, 2000

[54] RECOMBINANT NEW CASTLE DISEASE VIRUS RNA EXPRESSION SYSTEMS AND VACCINES

[75] Inventors: Adolfo Garcia-Sastre, New York, N.Y.; Peter Palese, Leonia, N.J.

[73] Assignee: Mount Sinai School of Medicine, of the City University of New York, New York, N.Y.

[21] Appl. No.: 09/152,845

[22] Filed: Sep. 14, 1998

[51] Int. Cl.$^7$ .......................... A61K 39/17; A61K 39/00; A61K 39/12; A61K 39/21; C07H 21/04

[52] U.S. Cl. ..................... 424/214.1; 424/192.1; 424/199.1; 424/208.1; 536/23.4; 536/23.72; 536/24.1; 536/24.2

[58] Field of Search ................................ 536/24.1, 23.4, 536/23.72, 24.2; 424/192.1, 199.1, 208.1, 214.1

[56] References Cited

U.S. PATENT DOCUMENTS

| | | | |
|---|---|---|---|
| 5,166,057 | 11/1992 | Palese et al. ............................ | 435/69.1 |
| 5,716,821 | 2/1998 | Wertz et al. .......................... | 435/235.1 |

FOREIGN PATENT DOCUMENTS 0 702 085  3/1996  European Pat. Off. .

OTHER PUBLICATIONS

Fahey et al., Status of immune-based therapies in HIV infection and AIDS, Clin. exp. Immunol., vol. 88, pp. 1–5, especially p. 3, col. 2 to p. 4, column 1, Jan. 1992.

Collins et al., 1991, "Rescue of Synthetic Analogs of Respiratory Syncytial Virus Genomic RNA and Effect of Truncations and Mutations on the Expression of a Foreign Reporter Gene", Proc. Natl. Acad. Sci. USA 88:9663–9667.

Collins et al., 1996, "Parainfluenza Viruses", Fields Virology (Lippencott–Raven Publishers, Philadelphia) pp. 1205–1242.

De and Banerjee, 1985, "Requirements and Functions of Vesicular Stomatitis Virus L and NS Proteins in the Transcription Process In Vitro", Biochem. Biophys. Res. Comm. 126:40–49.

Dreher and Hall, 1988, "Mutational Analysis of the Sequence and Structural Requirements in Brome Mosaic Virus RNA for Minus Strand Promoter Activity", J. Mol. Biol. 201:31–40.

Dreher et al., 1984, "Mutant Viral RNAs Synthesized In Vitro Show Altered Aminoacylation and Replicase Template Activities", Nature 311:171–175.

Emerson and Yu, 1975, "Both NS and L Proteins Are Required for In Vitro RNA Synthesis by Vesicular Stomatitis Virus", J. Virol. 15:1348–1356.

Enami et al., 1990, "Introduction of Site–Specific Mutations into the Genome of Influenza Virus", Proc. Natl. Acad. Sci. USA 87:3802–3805.

Fahey, J. and Schooley, R., 1992, "Status of Immune–based Therapies in HIV Infection and AIDS" Clin. Exp. Immunol. 88:1–5.

(List continued on next page.)

*Primary Examiner*—Hankyel Park
*Attorney, Agent, or Firm*—Pennie & Edmonds LLP

[57] ABSTRACT

This invention relates to genetically engineered Newcastle disease viruses and viral vectors which express heterologous genes or mutated Newcastle disease viral genes or a combination of viral genes derived from different strains of Newcastle disease virus. The invention relates to the construction and use of recombinant negative strand NDV viral RNA templates which may be used with viral RNA-directed RNA polymerase to express heterologous gene products in appropriate host cells and/or to rescue the heterologous gene in virus particles. In a specific embodiment of the invention, the heterologous gene product is a peptide or protein derived from the genome of a human immunodeficiency virus. The RNA templates of the present invention may be prepared by transcription of appropriate DNA sequences using a DNA-directed RNA polymerase such as bacteriophage T7, T3 or the SP6 polymerase.

14 Claims, 8 Drawing Sheets

OTHER PUBLICATIONS

Kaplan et al., 1985, "In Vitro Synthesis of Infectious Poliovirus RNA", Proc. Natl. Acad. Sci. USA 82:8424–8428.

Kato et al., "Initiation of Sendai Virus Multiplication from Transfected cDNA or RNA with Negative or Positive Sense", Genes Cells (1996) 1:569–579.

Krystal et al., "Expression of The Three Influenza Virus Polymerase Proteins in a Single Cell Allows Growth Complementation of Viral Mutants", 1986, Proc. Natl. Acad. Sci. USA 83:2709–2713.

Kunkel, 1985, "Rapid and Efficient Site–Specific Mutagenesis without Phenotypic Selection", Proc. Natl. Acad. Sci. USA 82:488.

Levis et al., 1986, "Deletion Mapping of Sindbis Virus DI RNAs Derived from cDNAs Defines the Sequences Essential for Replication and Packaging", Cell 44:137–45.

Luytjes et al., 1989, "Amplification, Expression, and Packaging of a Foreign Gene by Influenza Virus", Cell 59:1107–1113.

Naito and Ishihama, 1976, "Function and Structure of RNA Polymerase from Vesicular Stomatitis Virus", J. Biol. Chem. 251:4307–4314.

Nara et al., 1987, "Simple, Rapid, Quantitative, Syncytium–Forming Microassay for the Detection of Human Immunodeficiency Virus Neutralizing Antibody", AIDS Res. Hum. Retroviruses 3:283–302.

Park et al., 1991, Rescue of a Foreign Gene by Sendai Virus, Proc. Natl. Acad. Sci. USA 88:5537–5541.

Roberts, A and Rose, J., 1998, "Recovery of Negative–Strand RNA Virus from Plasmid DNAs: A Positive Approach Revitilizes a Negative Field", Virology 247:1–6.

Racaniello et al., 1981, "Cloned Poliovirus Complementary DNA is Infectious in Mammalian Cells", Science 214:916–919.

Schnell et al., 1994, "Infectious Rabies Viruses from Cloned cDNA", EMBO J. 13:4195–2033.

Szewczyk et al., 1988, "Purification, Thioredoxin Renaturation, and Reconstituted Activity of The Three Subunits of the Influenza A Virus RNA Polymerase", Proc. Natl. Acad. Sci. USA 85:7907–7911.

Taylor et al., 1990, "Newcastle Disease Virus Fusion Protein Expressed in a Fowlpox Virus Recombinant Confers Protection in Chickens", J. Virol. 64:1441–1450.

Yusoff K. et al., 1987, "Nucleotide Sequence Analysis of the L Gene of Newcastle Disease Virus: Homologies with Sendi and Vesicular Stomatitis Viruses" Nucleic Acids Res. 15: 3961–76.

Ward et al., 1988, "Direct Measurement of the Poliovirus RNA Polymerase Error Frequency In Vitro", J. Virol. 62:558–562.

Zaghouani et al., 1992, "Cells Expressing an H Chain Ig Gene Carrying a Viral T Cell Epitope Are Lysed by Specific Cytolytic T Cells", J. Immunol. 148:3604–3609.

Zaghouani et al., "Cells Expressing an H Chain Ig Gene Carrying a Viral T Cell Epitope Are Lysed by Specific Cytolytic T Cells", 1991, Proc. Natl. Acad. Sci. USA 88:5645–6549.

5'ACCAAACAGAGAAUCCGUAAGGUACGUUAAAAAGCGAAGGAGCAAUUGAAGUCGCACGGG
UAGAAGGUGUGAAUCUCGAGUGCGAGCCCGAAGCACAAACUCGAGAAAGCCUUCUACCAAC-
- - - - - - - - - - - - - - - - - - - -CAT gene (667 nt)- - - - - - - - - - - - - - - - - - -cuuaa
CGACAAUCACAUAUUAAUAGGCUCCUUUUCUGGCCAAUUGUAUCCUUGUUGAUUUAAUCAUA
CUAUGUUAGAAAAAAGUUGAACUCCGACUCCUUAGGACUCGAACUCGAACUCAAAUAAAUGU
CUUAGAAAAAGAUUGCGCACAGUUAUUCUUGAGUGUAGUCUUGUCAUUCACCAAAUCUUUGU
UUGGU-3'

FIG.3

```
1  TGGTTTGTCTCTTAGGCATTCCATGCAATTTTTCGCTTCCTCGTTAACTT  50
1  TGGTTTGTCTCTTAGGCATTCCATGCTATTTTCCGCTTCCTCGTTAACTT  50
   *************************  *****  *****************

51 CA---TGCCCATCTTCC  64
51 CAGCATGCCCATCTTCC  67
   **     ***********
```

FIG.5

RECOMBINANT NEW CASTLE DISEASE VIRUS RNA EXPRESSION SYSTEMS AND VACCINES

The invention was made with government support under grant numbers 97308MI and 73054MI awarded by the National Institutes of Health. The Government has certain rights in these inventions.

INTRODUCTION

The present invention relates to recombinant Newcastle disease virus RNA templates which may be used to express heterologous gene products in appropriate host cell systems and/or to construct recombinant viruses that express, package, and/or present the heterologous gene product. The expression products and chimeric viruses may advantageously be used in vaccine formulations.

The present invention relates to recombinant Newcastle disease viruses which induce interferon and related pathways. The present invention relates to the use of the recombinant Newcastle disease viruses and viral vectors against a broad range of pathogens and/or antigens, including tumor specific antigens. The invention is demonstrated by way of examples in which recombinant Newcastle disease virus RNA templates containing heterologous gene coding sequences in the negative-polarity were constructed. The invention further relates to the construction of recombinant Newcastle disease virus RNA templates containing heterologous gene coding sequences in the positive-polarity. Such heterologous gene sequences include sequences derived from a human immunodeficiency virus (HIV).

BACKGROUND OF THE INVENTION

A number of DNA viruses have been genetically engineered to direct the expression of heterologous proteins in host cell systems (e.g., vaccinia virus, baculovirus, etc.). Recently, similar advances have been made with positive-strand RNA viruses (e.g., poliovirus). The expression products of these constructs, i.e., the heterologous gene product or the chimeric virus which expresses the heterologous gene product, are thought to be potentially useful in vaccine formulations (either subunit or whole virus vaccines). One drawback to the use of viruses such as vaccinia for constructing recombinant or chimeric viruses for use in vaccines is the lack of variation in its major epitopes. This lack of variability in the viral strains places strict limitations on the repeated use of chimeric vaccinia, in that multiple vaccinations will generate host-resistance to the strain so that the inoculated virus cannot infect the host. Inoculation of a resistant individual with chimeric vaccinia will, therefore, not induce immune stimulation.

By contrast, the negative-strand RNA viruses, would be attractive candidates for constructing chimeric viruses for use in vaccines. The negative-strand RNA virus, influenza, for example is desirable because its wide genetic variability allows for the construction of a vast repertoire of vaccine formulations which stimulate immunity without risk of developing a tolerance. Recently, construction of infectious recombinant or chimeric negative-strand RNA particles was achieved with the influenza virus (U.S. Pat. No. 5,166,057 to Palese et al., incorporated herein by reference in its entirety).

The Newcastle Disease Virus

Virus families containing enveloped single-stranded RNA of the negative-sense genome are classified into groups having non-segmented genomes (Paramyxoviridae, Rhabdoviridae) or those having segmented genomes (Orthomyxoviridae, Bunyaviridae and Arenaviridae). The Paramyxoviridae family, described in detail below, and used in the examples herein, contain the viruses of Newcastle disease Virus (NDV), parainfluenza virus, Sendai virus, simian virus 5, and mumps virus.

The Newcastle disease Virus is an enveloped virus containing a linear, single-strand, nonsegmented, negative sense RNA genome. The genomic RNA contains genes in the order of 3'-NP-P-M-F-HN-L, described in further detail below. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrude from the envelope allowing the virus to contain both hemagglutinin and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the virus can not synthesize the required RNA-dependent RNA polymerase. The L, P and NP proteins must enter the cell along with the genome on infection.

It is hypothesized that most or all of the viral proteins that transcribe NDV mRNA also carry out their replication. The mechanism that regulates the alternative uses (i.e., transcription or replication) of the same complement of proteins has not been clearly identified but appears to involve the abundance of free forms of one or more of the nucleocapsid proteins, in particular, the NP. Directly following penetration of the virus, transcription is initiated by the L protein using the negative-sense RNA in the nucleocapsid as a template. Viral RNA synthesis is regulated such that it produces monocistronic mRNAs during transcription.

Following transcription, virus genome replication is the second essential event in infection by negative-strand RNA viruses. As with other negative-strand RNA viruses, virus genome replication in Newcastle disease virus (NDV) is mediated by virus-specified proteins. The first products of replicative RNA synthesis are complementary copies (i.e., plus-polarity) of NDV genome RNA (cRNA). These plusstranded copies (anti-genomes) differ from the plus-strand mRNA transcripts in the structure of their termini. Unlike the mRNA transcripts, the anti-genomic cRNAs are not capped and methylated at the 5' termini, and are not truncated and polyadenylated at the 3' termini. The cRNAs are coterminal with their negative strand templates and contain all the genetic information in each genomic RNA segment in the complementary form. The cRNAs serve as templates for the synthesis of NDV negative-strand viral genomes (vRNAs).

Both the NDV negative strand genomes (vRNAs) and antigenomes (cRNAs) are encapsidated by nucleocapsid proteins; the only unencapsidated RNA species are virus mRNAs. For NDV, the cytoplasm is the site of virus RNA replication, just as it is the site for transcription. Assembly of the viral components appears to take place at the host cell plasma membrane and mature virus is released by budding.

Engineering Negative Strand RNA Viruses

The RNA-directed RNA polymerases of animal viruses have been extensively studied with regard to many aspects of protein structure and reaction conditions. However, the elements of the template RNA which promote optimal expression by the polymerase could only be studied by inference using existing viral RNA sequences. This promoter analysis is of interest since it is unknown how a viral polymerase recognizes specific viral RNAs from among the many host-encoded RNAs found in an infected cell.

Animal viruses containing plus-sense genome RNA can be replicated when plasmid-derived RNA is introduced into cells by transfection (for example, Racaniello et al., 1981, Science 214:916–919; Levis, et al., 1986, Cell 44: 137–145). In the case of poliovirus, the purified polymerase will replicate a genome RNA in vitro reactions and when this preparation is transfected into cells it is infectious (Kaplan, et al., 1985, Proc. Natl. Acad. Sci. USA 82:8424–8428). However, the template elements which serve as transcription promoter for the poliovirus-encoded polymerase are unknown since even RNA homopolymers can be copied (Ward, et al., 1988, J. Virol. 62: 558–562). SP6 transcripts have also been used to produce model defective interfering (DI) RNAs for the Sindbis viral genome. When the RNA is introduced into infected cells, it is replicated and packaged. The RNA sequences which were responsible for both recognition by the Sindbis viral polymerase and packaging of the genome into virus particles were shown to be within 162 nucleotides (nt) of the 5' terminus and 19 nt of the 3' terminus of the genome (Levis, et al., 1986, Cell 44: 137–145). In the case of brome mosaic virus (BMV), a positive strand RNA plant virus, SP6 transcripts have been used to identify the promoter as a 134 nt tRNA-like 3' terminus (Dreher, and Hall, 1988, J. Mol. Biol. 201: 31–40). Polymerase recognition and synthesis were shown to be dependent on both sequence and secondary structural features (Dreher, et al., 1984, Nature 311: 171–175).

The negative-sense RNA viruses have been refractory to study of the sequence requirements of the replicase. The purified polymerase of vesicular stomatitis virus is only active in transcription when virus-derived ribonucleoprotein complexes (RNPs) are included as template (De and Banerjee, 1985, Biochem. Biophys. Res. Commun. 126: 40–49; Emerson and Yu, 1975, J. Virol. 15: 1348–1356; Naito, and Ishihama, 1976, J. Biol. Chem. 251: 4307–4314). With regard to influenza viruses, it was reported that naked RNA purified from virus was used to reconstitute RNPs. The viral nucleocapsid and polymerase proteins were gel-purified and renatured on the viral RNA using thioredoxin (Szewczyk, et al., 1988, Proc. Natl. Acad. Sci. USA, 85: 7907–7911). However, these authors did not show that the activity of the preparation was specific for influenza viral RNA, nor did they analyze the signals which promote transcription.

Only recently has it been possible to recover negative strand RNA viruses using a recombinant reverse genetics approach (U.S. Pat. No. 5,166,057 to Palese et al.). Although this method was originally applied to engineer influenza viral genomes (Luytjes et al. 1989, Cell 59: 1107–1113; Enami et al. 1990, Proc. Natl. Acad Sci. USA 92: 11563–11567), it has been successfully applied to a wide variety of segmented and nonsegmented negative strand RNA viruses, including rabies (Schnell et al. 1994, EMBO J. 13:4195–4203); respiratory syncytial virus (Collins et al. 1991, Proc. Natl. Acad. Sci. USA 88:9663–9667); and Sendai virus (Park et al. 1991, Proc. Natl. Acad. Sci. USA 88:5537–5541; Kato et al., 1996, Genes Cells 1:569–579). However, this approach has yet to be applied to Newcastle disease virus RNA genomes.

SUMMARY OF THE INVENTION

Recombinant Newcastle disease viral RNA templates are described which may be used with RNA-directed RNA polymerase to express heterologous gene products in appropriate host cells and/or to rescue the heterologous gene in virus particles. In one embodiment, the invention relates to recombinant Newcastle disease viruses which induce interferon and related pathways. In another embodiment, the present invention relates to engineering recombinant Newcastle disease viruses and viral vectors which contain heterologous genes including genes of other viruses, pathogens, cellular genes, tumor antigens etc.

In another embodiment, the present invention relates to engineering recombinant Newcastle disease viruses and viral vectors for the use as vaccines. In yet another embodiment, the invention relates to recombinant Newcastle disease viral vectors and viruses which are engineered to encode mutant Newcastle disease viral genes or to encode combinations of genes from different strains of Newcastle disease virus.

The RNA templates of the present are prepared by transcription of appropriate DNA sequences with a DNA-directed RNA polymerase. The resulting RNA templates are of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Expression from positive polarity RNA templates may be achieved by transfection of plasmids having promoters which are recognized by the DNA-dependent RNA polymerase. For example, positive RNA templates can be used in combination with the vaccinia virus T7 system.

Bicistronic mRNAs can be constructed to permit internal initiation of translation of viral sequences and allow for the expression of foreign protein coding sequences from the regular terminal initiation site, or vice versa. Alternatively, a foreign protein may be expressed from internal transcriptional unit in which the transcriptional unit has an initiation site and polyadenylation site. In another embodiment, the foreign gene is inserted into an NDV gene such that the resulting expressed protein is a fusion protein.

The recombinant mutant Newcastle disease viral RNA templates of the present invention may be used to transfect transformed cell lines that express the RNA dependent RNA-polymerase and allow for complementation. Alternatively, a plasmid expressing from an appropriate promoter, can be used for virus specific (chimeric) RNA transfection. Complementation may also be achieved with the use of a helper virus which provides the RNA dependent RNA-polymerase.

Additionally, a non-virus dependent replication system for Newcastle disease virus is also described. The minimum subset of Newcastle disease virus protein needed for specific replication and expression of the virus are the three proteins, L, P and NP, which can be expressed from plasmids by a vaccinia virus T7 system.

The expression products and/or chimeric virions obtained may advantageously be utilized in vaccine formulations. The expression products and chimeric virions of the present invention may be engineered to create vaccines against a broad range of pathogens, including viral antigens, tumor antigens and auto antigens involved in autoimmune disorders. In particular, the chimeric virions of the present invention may be engineered to create anti-HIV vaccines, wherein an immunogenic polypeptide from gp160, and/or from internal proteins of HIV is engineered into the glycoprotein HN protein to construct a vaccine that is able to elicit both vertebrate humoral and cell-mediated immune responses. The use of recombinant Newcastle disease virus for this purpose is especially attractive since Newcastle disease virus is not pathogenic in humans. The use of recombinant Newcastle disease virus for delivering tumor antigens is particularly attractive given the known antineoplastic and immunopotentiating properties of the virus.

Definitions

As used herein, the following terms will have the meanings indicated:

cRNA=anti-genomic RNA
HIV=human immunodefiency virus
L=large protein
M=matrix protein (lines inside of envelope)
MDCK=Madin Darby canine kidney cells
MDBK=Madin Darby bovine kidney cells
moi=multiplicity of infection
NA=neuraminidase (envelope glycoprotein)
NDV=Newcastle disease Virus
NP=nucleoprotein (associated with RNA and required for polymerase activity)
NS=nonstructural protein (function unknown)
nt=nucleotide
PA, PB1, PB2=RNA-directed RNA polymerase components
RNP=ribonucleoprotein (RNA, PB2, PB1, PA and NP)
rRNP=recombinant RNP
vRNA=genomic virus RNA
viral polymerase complex=PA, PB1, PB2 and NP
WSN=influenza A/WSN/33 virus
WSN-HK virus: reassortment virus containing seven genes from WSN virus and the NA gene from influenza A/HK/8/68 virus

PTM1-NP encodes the NDV NP protein.
PTM1-P encodes the NDV P protein.
PTM1-L encodes the NDV L protein.

FIG. 3. RNA sequence of NDV 5' and 3' non-coding terminal regions (plus-sense). Sequences 5' to the CAT gene represent 121 nt of the 5' non-coding terminal region of NDV plus sense genome comprising 65 nt of the leader sequence (in bold) followed by 56 nt of the NP gene UTR (SEQ ID NO:1). Sequences 3' to the CAT gene represent inserted nucleotides cuuaa (in lower case) and 191 nt of the non-coding terminal region of NDV plus sense genome comprising 127 nt of the UTR of the L gene followed by 64 nt of the trailer region (in bold) (SEQ ID NO:2).

Figure 4A:
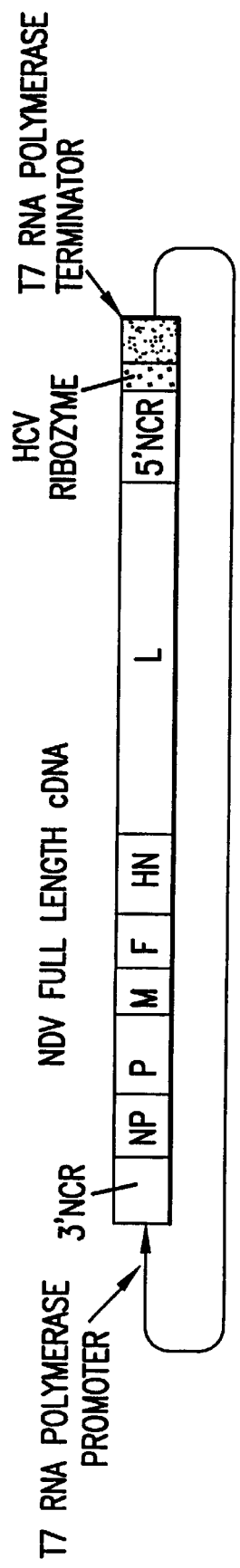
Figure 4B:
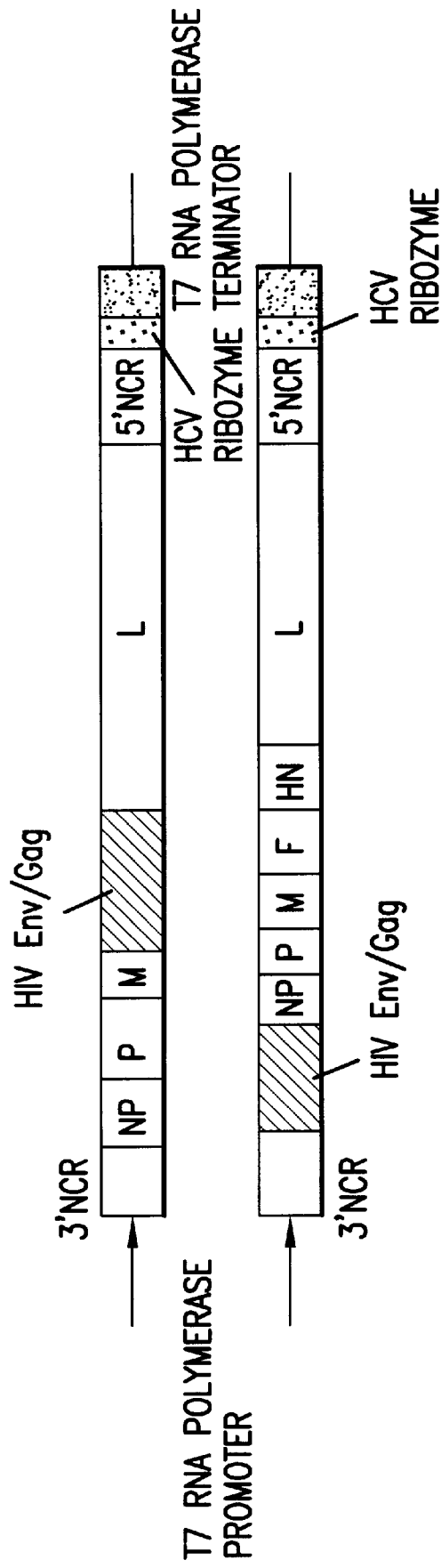

FIGS. 4A–B Schematic representation of a structure of recombinant NDV clones. FIG. 4B, representation of infectious NDV expressing HIV Env and Gag. Top panel, HIV Env and Gag are between the M and L genes. Lower panel, HIV Env and Gag are 3' to the NP gene.

FIG. 5 Schematic representation of the 3'termini of NDV (SEQ ID NO:3) as aligned with sequence of Collins et al. (SEQ ID NO:4) Parainfluenza viruses, in Field's Virology, 3rd ed. B. N. Fields, D. M. Knipe, p. m. Howley et al, eds., Lippincott-Raven Publishing, Philidalphia, 1996.

DESCRIPTION OF THE INVENTION

This invention relates to genetically engineered Newcastle disease viruses and viral vectors which express heterologous genes or mutated Newcastle disease viral genes or a combination of viral genes derived from different strains of Newcastle disease virus. The invention relates to the construction and use of recombinant negative strand NDV viral RNA templates which may be used with viral RNA-directed RNA polymerase to express heterologous gene products in appropriate host cells and/or to rescue the heterologous gene in virus particles. In a specific embodiment of the invention, the heterologous gene product is a peptide or protein derived from the genome of a human immunodeficiency virus. The RNA templates of the present invention may be prepared by transcription of appropriate DNA sequences using a DNA-directed RNA polymerase such as bacteriophage T7, T3 or the SP6 polymerase.

The recombinant RNA templates may be used to transfect continuous/transfected cell lines that express the RNA-directed RNA polymerase proteins allowing for complementation.

The invention is demonstrated by way of working examples in which RNA transcripts of cloned DNA containing the coding region—in negative sense orientation—of the chloramphenicol acetyltransferase (CAT) gene, flanked by the 5' terminal and the 3' terminal nucleotides of the NDV California strain-11914-1944 RNA were transfected into cells expressing the NDV polymerase proteins.

The ability to reconstitute NDV in vivo allows the design of novel chimeric NDV viruses which express foreign genes or which express mutant NDV genes. The ability to reconstitute NDV in vivo also allows the design of novel chimeric NDVs which express genes from different strains of NDV. One way to achieve this goal involves modifying existing NDV genes. For example, the HN gene may be modified to contain foreign sequences in its external domains. Where the heterologous sequence are epitopes or antigens of pathogens, these chimeric viruses may be used to induce a protective immune response against the disease agent from which these determinants are derived.

The present invention relates to the use of viral vectors and chimeric viruses of the invention to formulate vaccines against a broad range of viruses and/or antigens including tumor antigens. The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs goats, dogs, cats, chickens and rodents. When delivering, tumor antigens, the invention may be used to treat subjects having disease amenable to immunity mediated rejection, such as non-solid tumors or solid tumors of small size. It is also contemplated that delivery of tumor antigens by the viral vectors and chimeric viruses described herein will be useful for treatment subsequent to removal of large solid tumors. The invention may also be used to treat subjects who are suspected of having cancer.

In accordance with the present invention, a chimeric RNA is constructed in which a coding sequence derived from the gp160 coding region of human immunodeficiency virus is inserted into the HN coding sequence of NDV, and chimeric virus produced from transfection of this chimeric RNA segment into a host cell infected with wild-type NDV. Further, such a chimeric virus should be capable of eliciting both a vertebrate humoral and cell-mediated immune response. The present invention further relates to the induction of interferon and related pathways by recombinant or chimeric NDV viruses.

The invention may be divided into the following stages solely for the purpose of description and not by way of limitation: (a) construction of recombinant RNA templates; (b) expression of heterologous gene products using the recombinant RNA templates; and (c) rescue of the heterologous gene in recombinant virus particles. For clarity of discussion, the invention is described in the working Examples using NDV California strain-11914-1944, however any strain of NDV may be utilized. The recombinant RNA templates, viral vectors and chimeric viruses of the present invention may be constructed using the materials and methods described in U.S. Pat. No. 5,166,057 to Palese et al., incorporated herein by reference in its entirety.

Construction of the Recombinant RNA Templates

A specific embodiment of the present invention is the Applicants' identification of the correct nucleotide sequence of the 5' and 3' termini of the negative-sense genomes RNA of NDV. The nucleotide sequence of the 3' termini of the NDV negative-sense genome RNA of the present invention differs significantly from the NDV 3' termini sequence previously disclosed by Collins et al. in Fundamental Virology 3rd Ed. 1996 by Lippincott-Raven Publishers as shown in FIG. 5. The identification of the correct nucleotide sequence of the NDV 3' termini allows for the first time the engineering of recombinant NDV RNA templates, the expression of the recombinant RNA templates and the rescue of recombinant NDV particles.

Heterologous gene coding sequences flanked by the complement of the viral polymerase binding site/promoter, e.q, the complement of 3'-NDV virus terminus of the present invention, or the complements of both the 3'- and 5'-NDV virus termini may be constructed using techniques known in the art. The resulting RNA templates may be of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Recombinant DNA molecules containing these hybrid sequences can be cloned and transcribed by a DNA-directed RNA polymerase, such as bacteriophage T7, T3, or the SP6 polymerase and the like, to produce in vitro and in vivo the recombinant RNA templates which possess the appropriate viral sequences that allow for viral polymerase recognition and activity.

In yet another embodiment, heterologous sequences which may be engineered into the chimeric viruses of the present invention fall into four classes: 1) antigens that are characteristic of a pathogen; 2) antigens that are characteristic of autoimmune disease; 3) antigens that are characteristic of an allergen; and 4) antigens that are characteristic of a tumor. For example, heterologous gene sequences that can be engineered into the chimeric viruses of the invention include, but are not limited to, epitopes of human immunodeficiency virus (HIV) such as gp160; hepatitis B virus surface antigen (HBsAg); the glycoproteins of herpes virus (e.g., gD, gE); VP1 of poliovirus; and antigenic determinants of nonviral pathogens such as bacteria and parasites to name but a few.

Antigens that are characteristic of autoimmune disease typically will be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discold lupus erythromatosus.

Antigens that are allergens are generally proteins or glycoproteins, including antigens derived from pollens, dust, molds, spores, dander, insects and foods.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within an NDV gene coding sequence such that a chimeric gene product is expressed which contains the heterologous peptide sequence within the NDV viral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

One approach for constructing these hybrid molecules is to insert the heterologous coding sequence into a DNA complement of an NDV gene so that the heterologous sequence is flanked by the viral sequences required for viral polymerase activity; i.e., the viral polymerase binding site/promoter, hereinafter referred to as the viral polymerase binding site, and a polyadenylation site. In an alternative approach, oligonucleotides encoding the viral polymerase binding site, e.g., the complement of the 3'-terminus or both termini of the virus genomic segments can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82;488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophase T3, T7 or SP6) and the hybrid sequence containing the heterologous gene and the NDV polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase. Sequence requirements for viral polymerase activity and constructs which may be used in accordance with the invention are described in the subsections below.

Insertion of the Heterologous Gene Sequence Into the HN, P, NP, M, F, L Genes The gene segments coding for the HN, P, NP, M, F, or L proteins may be used for the insertion of heterologeous gene products. Insertion of a foreign gene sequence into any of these segments could be accomplished by either a complete replacement of the viral coding region with the foreign gene or by a partial replacement. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the NDV gene; and a stretch of nucleotides complementary to the carboxy-terminus coding portion of the foreign gene product. PCR-primer B would contain from the 5' to 3' end: a unique restriction enzyme site; a stretch of nucleotides complementary to a NDV gene; and a stretch of nucleotides corresponding to the 5' coding portion of the foreign gene. After a PCR reaction using these primers with a cloned copy of the foreign gene, the product may be excised and cloned using the unique restriction sites. Digestion with the class IIS enzyme and transcription with the purified phage polymerase would generate an RNA molecule containing the exact untranslated ends of the NDV gene with a foreign gene insertion. In an alternate embodiment, PCR-primed reactions could be used to prepare double-stranded DNA containing the bacteriophage promoter sequence, and the hybrid gene sequence so that RNA templates can be transcribed directly without cloning.

Insertion of the Heterologous Gene Sequence Into the HN Gene

The hemagglutinin and neuraminidase activities of NDV are coded for by a single gene, HN. The HN protein is a major surface glycoprotein of the virus. For a variety of viruses, such as influenza, the hemagglutinin and neuraminidase proteins have been demonstrated to contain a number of antigenic sites. Consequently, this protein is a potential target for the humoral immune response after infection. Therefore, substitution of antigenic sites within HN with a portion of a foreign protein may provide for a vigorous humoral response against this foreign peptide. If a sequence is inserted within the HN molecule and it is expressed on the outside surface of the HN it will be immunogenic. For example, a peptide derived from gp160 of HIV could be inserted into antigenic site of the HN protein for antigenic presentation by the chimeric virus, resulting in the elicitation of both a humoral immune response. In a different approach, the foreign peptide sequence may be inserted within the antigenic site without deleting any viral sequences. Expression products of such constructs may be useful in vaccines against the foreign antigen, and may indeed circumvent a problem discussed earlier, that of propagation of the recombinant virus in the vaccinated host. An intact HN molecule with a substitution only in antigenic sites may allow for HN function and thus allow for the construction of a viable virus. Therefore, this virus can be grown without the need for additional helper functions. The virus may also be attenuated in other ways to avoid any danger of accidental escape.

Other hybrid constructions may be made to express proteins on the cell surface or enable them to be released from the cell. As a surface glycoprotein, the HN has an amino-terminal cleavable signal sequence necessary for transport to the cell surface, and a carboxy-terminal sequence necessary for membrane anchoring. In order to express an intact foreign protein on the cell surface it may be necessary to use these HN signals to create a hybrid protein. In this case, the fusion protein may be expressed as a separate fusion protein from an additional internal promoter. Alternatively, if only the transport signals are present and the membrane anchoring domain is absent, the protein may be secreted out of the cell.

Construction of Bicistronic RNA and Heterologous Protein Expression

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with Newcastle disease virus packaging limitations. Thus, it is preferable that the IRES chosen for such a bicistronic approach be no more than 500 nucleotides in length, with less than 250 nucleotides being preferred. Further, it is preferable that the IRES utilized not share sequence or structural homology with picornaviral elements. Preferred IRES elements include, but are not limited to the mammalian BiP IRES and the hepatitis C virus IRES.

Alternatively, a foreign protein may be expressed from an internal transcriptional unit in which the transcriptional unit has an initiation site and polyadenylation site. In another embodiment, the foreign gene is inserted into an NDV gene such that the resulting expressed protein is a fusion protein.

Expression of Heterologous Gene Products Using Recombinant RNA Template

The recombinant templates prepared as described above can be used in a variety of ways to express the heterologous gene products in appropriate host cells or to create chimeric viruses that express the heterologous gene products. In one embodiment, the recombinant template can be used to transfect appropriate host cells, may direct the expression of the heterologous gene product at high levels. Host cell systems which provide for high levels of expression include continuous cell lines that supply viral functions such as cell lines superinfected with NDV, cell lines engineered to complement NDV functions, etc.

In an alternate embodiment of the invention, the recombinant templates may be used to transfect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions such as NP or HN.

In another embodiment, a helper virus may provide the RNA polymerase protein utilized by the cells in order to achieve expression of the heterologous gene product.

Figure 2A:
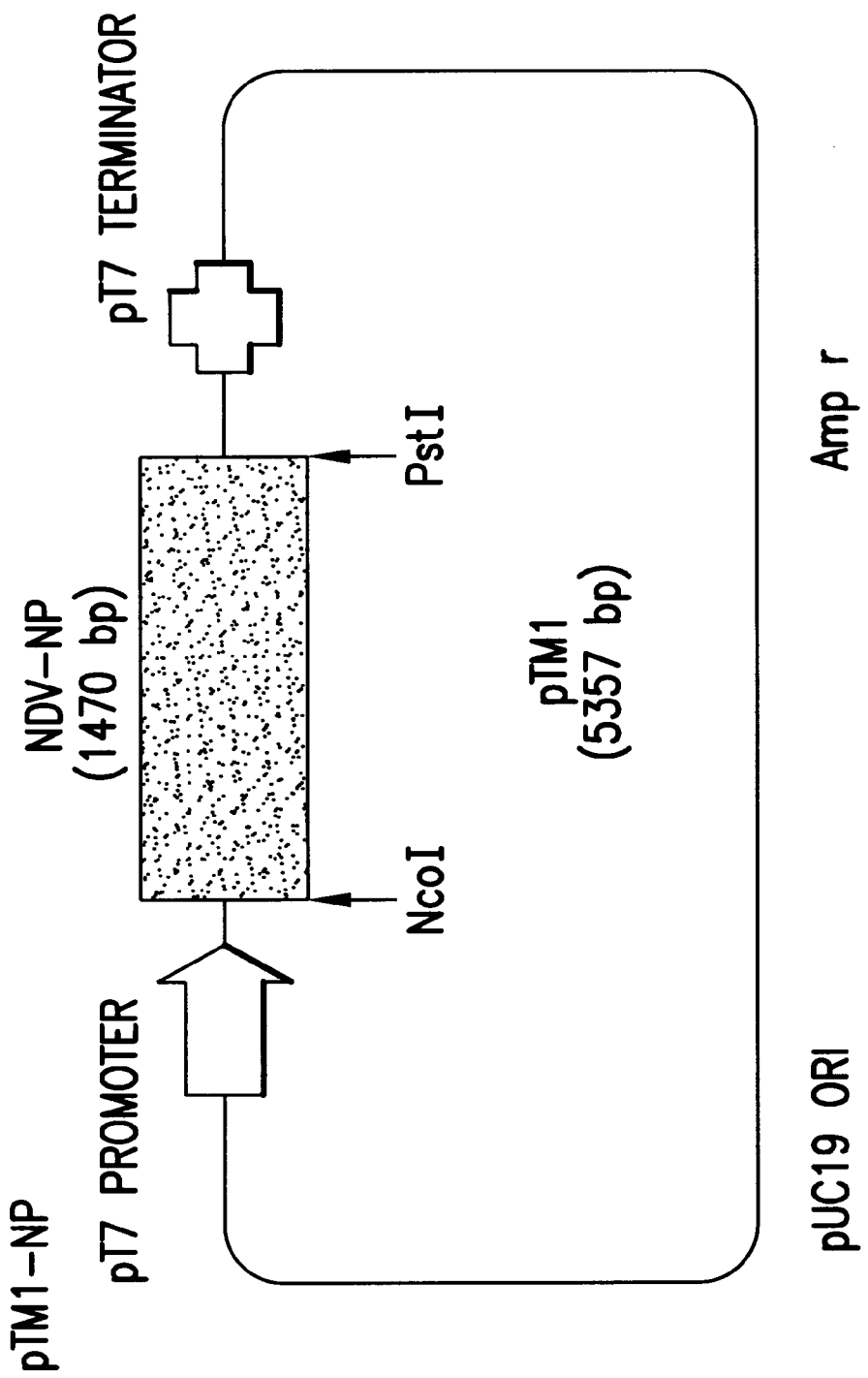
FIGS. 2A–C. Schematic representation of the PTMI expression vectors.
Figure 2B:
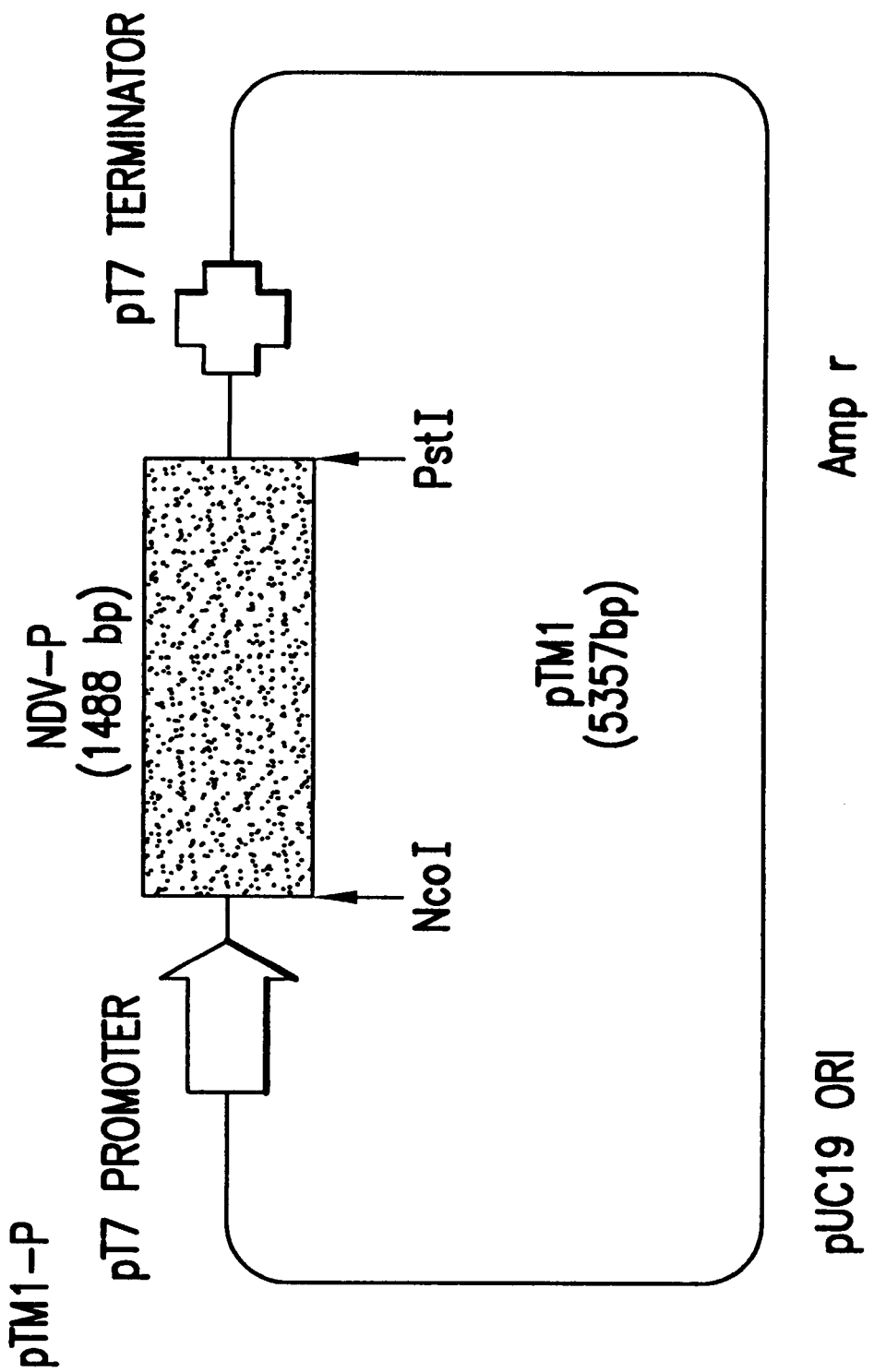
Figure 2C:
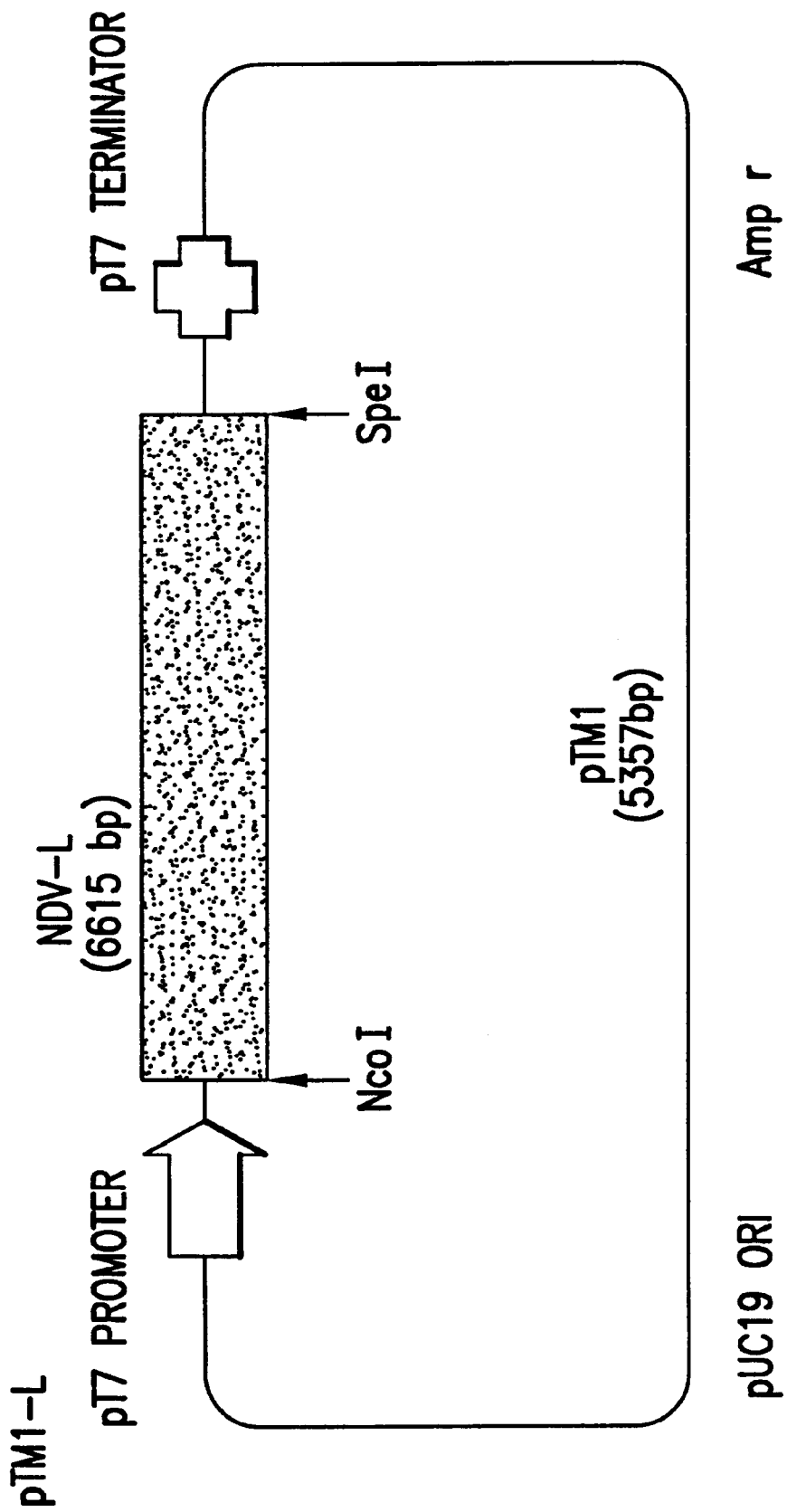

In yet another embodiment, cells may be transfected with vectors encoding viral proteins such as the NP, P and L proteins. Examples of such vectors are illustrated in FIGS. 2A–2C.

Preparation of Chimeric Negative Strand RNA Virus

In order to prepare chimeric virus, containing modified NDV virus RNAs or RNA coding for foreign proteins in the plus or minus sense, may be used to transfect cells which are also infected with a "parent" NDV virus. Following reassortment, the novel viruses may be isolated and their genomes be identified through hybridization analysis. In additional approaches described herein the production of infectious chimeric virus may be replicated in host cell systems that express an NDV viral polymerase protein (e.g., in virus/host cell expression systems; transformed cell lines engineered to express a polymerase protein, etc.), so that infectious chimeric virus are rescued. In this instance, helper virus need not be utilized since this function is provided by the viral polymerase proteins expressed.

In a particularly desirable approach, cells engineered to express all NDV viral genes may result in the production of infectious chimeric virus which contain the desired genotype; thus eliminating the need for a selection system. Theoretically, one can replace any one of the six genes or part of any one of the six genes of NDV with a foreign sequence. However, a necessary part of this equation is the ability to propagate the defective virus (defective because a normal viral gene product is missing or altered). A number of possible approaches exist to circumvent this problem. In one approach a virus having a mutant protein can be grown in cell lines which are constricted to constitutively express the wild type version of the same protein. By this way, the cell line complements the mutation in the virus. Similar techniques may be used to construct transformed cell lines that constitutively express any of the NDV genes. These cell lines which are made to express the viral protein may be used to complement the defect in the recombinant virus and thereby propagate it. Alternatively, certain natural host range systems may be available to propagate recombinant virus.

A third approach to propagating the recombinant virus may involve co-cultivation with wild-type virus. This could be done by simply taking recombinant virus and co-infecting cells with this and another wild-type virus (preferably a vaccine strain). The wild-type virus should complement for the defective virus gene product and allow growth of both the wild-type and recombinant virus. Alternatively, a helper virus may be used to support propagation of the recombinant virus.

In another approach, synthetic templates may be replicated in cells co-infected with recombinant viruses that express the NDV virus polymerase protein. In fact, this method may be used to rescue recombinant infectious virus in accordance with the invention. To this end, the an NDV polymerase protein may be expressed in any expression vector/host cell system, including but not limited to viral expression vectors (e.g., vaccinia virus, adenovirus, baculovirus, etc.) or cell lines that express a polymerase protein (e.g., see Krystal et al., 1986, Proc. Natl. Acad. Sci. USA 83: 2709–2713). Moreover, infection of host cells expressing all six NDV proteins may result in the production of infectious chimeric virus particles. This system would eliminate the need for a selection system, as all recombinant virus produced would be of the desired genotype.

It should be noted that it may be possible to construct a recombinant virus without altering virus viability. These altered viruses would then be growth competent and would not need helper functions to replicate. For example, alterations in the hemagglutinin neuraminidase gene discussed, supra, may be used to construct such viable chimeric viruses.

In an examples infra, the construction of a recombinant plasmid is described that, following transcription by T7 polymerase, yielded an RNA template which was recognized and transcribed by the virus polymerase in vitro. This RNA template corresponds to the negative strand RNA of an NDV except that the viral coding sequences are replaced by those of a CAT gene. This recombinant negative strand viral RNA template was then transfected into cells which were expressing the NDV L, NP and P proteins, and infected with rVV, leading to expression of CAT activity.

Vaccine Formulations Using the Chimeric Viruses

Virtually any heterologous gene sequence may be constructed into the chimeric viruses of the invention for use in vaccines. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric NDV that may then be used to elicit a vertebrate immune response.

Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification. Additionally, as NDV has been demonstrated to be non-pathogenic in humans, this virus is highly suited for use as a live vaccine.

In this regard, the use of genetically engineered NDV (vectors) for vaccine purposes may desire the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the human host and cause disease. Recombinant viruses lacking one or more of the NDV genes or possessing mutated NDV genes would not be able to undergo successive rounds of replication. Defective viruses can be produced in cell lines which permanently express such a gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines. Alternatively, mutated NDV made from cDNA may be highly attenuated so that it replicates for only a few rounds.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or $\beta$-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG and Corynebacterium parvum.

Many methods may be used to introduce the vaccine formulations described above, these include but are not limited to oral, intradermal, intramuscular, intraperitoneal, intravenous, subcutaneous, and intranasal routes. It may be preferable to introduce the chimeric virus vaccine formulation via the natural route of infection of the pathogen for which the vaccine is designed.

EXAMPLE

Expression and Packaging of a Foreign Gene by Recombinant NDV

The expression of the chloramphenicol transferase gene (CAT) using the NDV minigenome is described. The NDV minigenome was prepared using pNDVCAT, a recombinant plasmid containing the CAT gene. The pNDVCAT plasmid is a pUC19 plasmid containing in sequence: the T7-promoter; the 5'-end of the NDV genomic RNA comprising 191 nucleotides of noncoding NDV RNA sequence; 5 inserted nucleotides (3'CTTAA); the complete coding sequence of the chloramphenicol transferase (CAT) gene in the reversed and complemented order; the 3'-end of the NDV genomic RNA sequence comprising 121 nucleotides of noncoding NDV RNA sequence; a BbsI cloning site and several restriction sites allowing run-off transcription of the template. The pNDVCAT can be transcribed using T7 polymerase to create an RNA with Newcastle disease viral-sense flanking sequences around a CAT gene in reversed orientation.

The length of a paramyxovirus RNA can be a major factor that determines the level of RNA replication, with genome replication being most efficient when the total number of nucleotides is a multiple of six. For NDV, the question of whether this rule of six is critical for replication was examined by generating CAT mini-replicons of varying lengths, differing by one to five nucleotides. Only one construct whose genome was divisible by six was able to induce high CAT activity.

Construction of the Newcastle Disease Virus Minigenome

Figure 1:
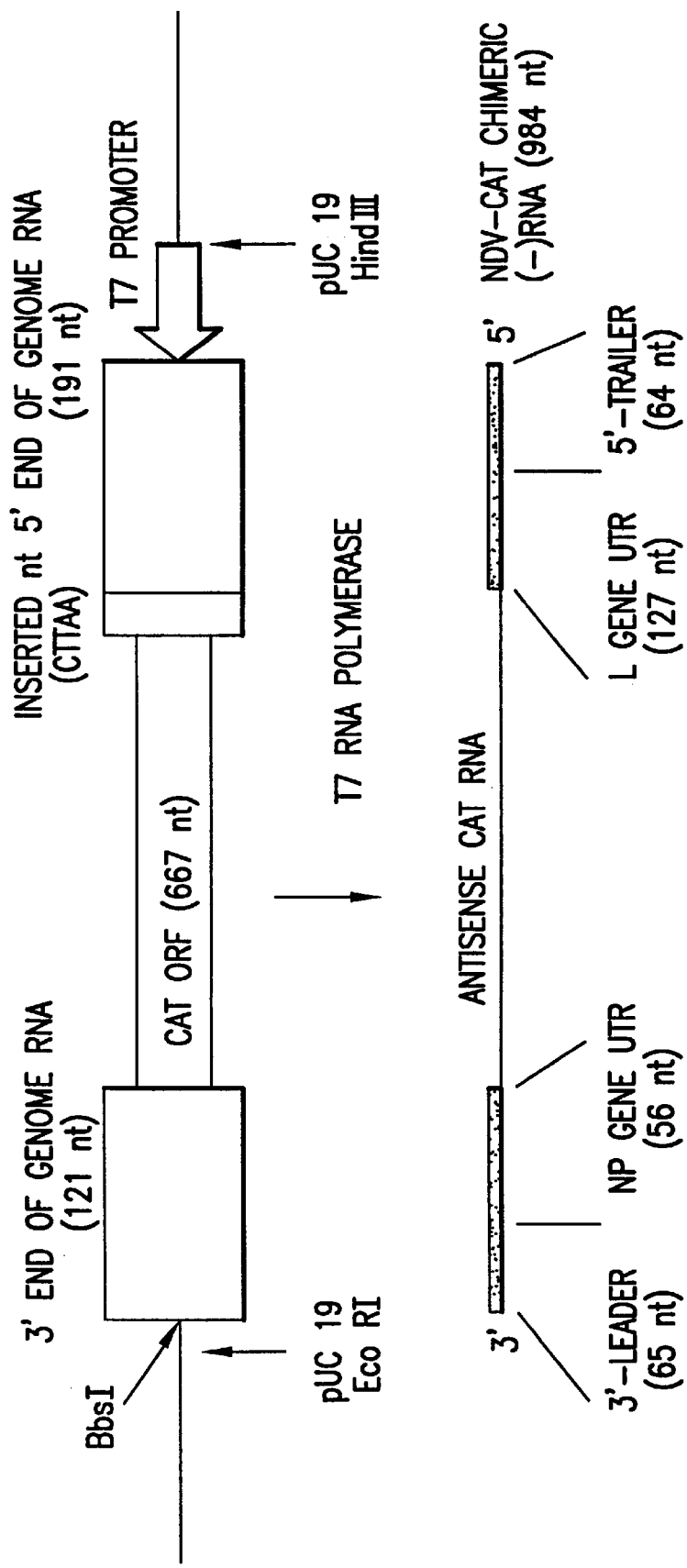
FIG. 1. Schematic representation of the NDV minigenome. Top illustration depicts the PNDVCAT plasmid including the T7 promoter; the 5' terminal sequence (5' end of genomic RNA, 191 nt); the inserted nucleotides (CTTAA); 667 nt of CAT ORF; the 3' terminal sequence (3' end of genomic RNA, 121 nt) the BbS1 and nuclease sites. Lower illustration depicts the chimeric NDV-CAT RNA resulting from in vitro transcription.

In order to construct an NDV minigenome, as described supra, the following strategy was used. The 5' terminal sequence of genomic NDV RNA was obtained by RACE (Gibco, BRL) using standard techniques in the art. The template for the RACE reaction was genomic RNA which was purified from NDV virions (strain: California-11914-1944). As illustrated in FIG. 3, this terminal sequence comprised 64 nucleotides of a trailer sequence plus 127 nucleotides of the untranslated region of the L gene. Located adjacent to the 191 viral nucleotide sequence, a 5 nucleotide sequence (3' CCTTAA) was inserted. A CAT gene comprised 667 nucleotides of the CAT open reading frame which was placed between the viral 5' and 3' terminal non-coding regions. In order to obtain the 3' terminal region of the NDV sequence, RT-PCR was used. The template for the RT-PCR reaction was in vitro polyadenylated genomic RNA of NDV. As illustrated in FIG. 3, the 3' terminal region of 121 nucleotides was comprised of 56 nucleotides of the untranslated region of the NP gene plus 65 nucleotides of a leader sequence. The resulting construct of the NDV minigenome is shown in FIG. 1. Nucleotide sequences of 3' and 5' non-coding terminal region shown in FIG. 3

Construction of the NDV NP, P & L Expression Plasmids

As described in Section 5, the transcription or replication of a negative strand RNA genome requires several protein components to be brought in with the virus, including the L protein, P protein and NP protein. In order to facilitate the expression from the NDV minigenome, the genes encoding each of the L, P and NP proteins were cloned into pTM1 expression vectors as illustrated in FIGS. 2A–C. The pTM1 expression vectors comprises a T7 promoter, several cloning sites for insertion of the gene of interest (L, P or NP), a T7 terminator, a pUC19 origin of replication and an ampicillin resistance gene. In order to construct the expression plasmids, full length DNA of NDV nucleoprotein (NP), phosphoprotein (P) and polymerase (L) were obtained by PCR amplification. These DNAs were cloned into T7 polymerase expression vector pTM1, respectively (FIGS. 2A–C).

RNA Transcription of the NDV Minigenome

RNA transcription from the NDV minigene plasmid was performed with the Ribomax kit (Promega) as specified by the manuscripts. In order to allow run-off transcription, 1 µg of NDV minigenome plasmid (pNDVCAT) was digested with Bbs I. The linearized plasmid was then used as a template of transcription reaction (for 2 hours at 37° C.). In order to remove template DNA, the resulting reaction mixture was treated with RNase-free DNase (for 15 min. at 37° C.) and purified by phenol-chloroform extraction, followed by ethanol precipitation.

Cell Transfections

Cos-1 cells, or 293T cells were grown on 35 mm dishes and infected with the helper virus rVV T7 at a multiplicity of infection (moi) of approximately 1 for 1 hour before transfection. The cells were then transfected with the expression vectors encoding the NP, P and L proteins of NDV. Specifically, transfections were performed with DOTAP (Boehringer Mannheim). Following helper virus infection, cells were transfected with the pTM1-NP (1 µg), pTM1-P (1 µg) and pTM1-L (0.1 µg) for 4 hours. Control transfections, lacking the L protein, were performed on a parallel set of cells with pTM1-NP (1 µg), pTM1-P (1 µg) and mock pTM1-L (0 µg). After the 4 hour incubation period, cells were subjected to RNA transfection with 0.5 µg of the NDV-CAT chimeric (−) RNA (see FIG. 1). Following RNA transfection, cells were allowed to incubate for 18 hours. The cell lysates were subsequently harvested for the CAT assay.

Cat Assays

CAT assays were done according to standard procedures, adapted from Gorman et al., 1982, Mol. Cell. Biol. 2: 1044–1051. The assays contained 10 µl of $^{14}$C chloramphenicol (0.5 µCi; 8.3 nM; NEN), 20 µl of 40 mM acetyl CoA (Boehringer) and 50 µl of cell extracts in 0.25 M Tris buffer (pH 7.5). Incubation times were 16–18 hours.

Results

In each cell line transfected with the NP, P, L expression vectors, and the chimeric NDV-CAT RNA, high levels of expression of CAT was obtained 18 hours post-infection. In addition, control transfected cells lacking the L protein did not express CAT.

Rescue of Infectious NDV Viruses Using RNA Derived From Specific Recombinant DNA The experiments described in the subsections below demonstrate the rescue of infectious NDV using RNA which is derived from specific recombinant DNAs. RNAs corresponding to the chimeric NDV-CAT RNA may be used to show that the 191 nucleotides of the 5' terminal and the 121 nucleotides of the 3' terminal nucleotides of the viral RNAs contain all the signals necessary for transcription, replication and packaging of model NDV RNAs. RNAs containing all the transcriptional units of the NDV genomes can be expressed from transfected plasmids. Thus, this technology allows the engineering of infectious NDV viruses using cDNA clones and site-specific mutagenesis of their genomes. Furthermore, this technology may allow for the construction of infectious chimeric NDV viruses which can be used as efficient vectors for gene expression in tissue culture, animals or man.

EXAMPLE

Recombinant Newcastle Disease Virus Containing an HIV Antigen gp160 Epitope Inserted into the NDV Genome In the Example presented herein, a chimeric NDV is constructed to express a heterologous antigen derived from gp160 of HIV. The experiments described in the subsections below demonstrate the use of a recombinant RNA template to generate a chimeric NDV that expresses a HIV gp160-derived peptide within the NDV genome and, further, this chimeric NDV is used to elicit a vertebrate humoral and cell-mediated immune response.

Construction of Plasmid

Recombinant NDV cDNA clones expressing HIV gp160 proteins may be constructed in a number of ways known in the art. For example, as illustrated in FIG. 4, the HIV Env and Gag proteins may be inserted into the NDV in a number of locations. In one example, the Env and Gag proteins are inserted between the M and L genes. In a different example, the Env and Gag proteins are inserted 3' to the NP gene (between the leader sequence and NP). Alternatively, these HIV proteins will be incorporated between the NDV envelope proteins (HN and F) at the 3' end. These protiens may also be inserted into or between any of the NDV genes.

Generation of Infectious Chimeric Virus

Transfection of RNA derived from plasmid comprising a recombinant NDV genome may be transfected into cells such as, for example, COS, 293 MDBK and selection of infectious chimeric virus may be done as previously described. See U.S. Pat. No. 5,166,057, incorporated herein by reference in its entirety. The resulting RNA may be transfected into cells infected with wild type virus by using standard transfection protocol procedures. Posttransfection, the supernatant may be collected and used at different dilutions to infect fresh cells in the presence of NDV antiserum. The supernatant may also be used for plaque assays in the presence of the same antiserum. The rescued virus can then be purified and characterized, and used, for example, in antibody production.

Hemagglutination Inhibition and Virus Neutralization Assays

Hemagglutination inhibition (HI) assays are performed as previously described (Palmer, D. F. et al., 1975, Immunol. Ser. 6:51–52). Monoclonal antibodies (2G9, 4B2, 2F1O, 25-5) are prepared by standard procedures with a human anti-gp120 monoclonal antibody. Ascites fluid containing monoclonal antibodies is treated with receptor-destroying enzyme as previously described (Palmer, D. F. et al., 1975, Immunol. Ser. 6:51–52).

For virus neutralization assay, cells in 30-mm-diameter dishes are infected virus. After a 1 h adsorption, agar overlay containing antibody at different dilutions is added. The cell monolayer is then stained with 0.1% crystal violet at 72 h postinfection.

Immunization 6 weeks old BALB/c mice are infected either via the aerosol route with the virus, or are immunized intraperitoneally (i.p.) with 10 $\mu$g of purified virus. For all booster immunizations, 10 $\mu$g of purified virus is administered i.p. Sera is collected 7 days after each immunization.

Radioimmunoassay

The radioimmunoassay is performed as previously described (Zaghouani, H. et al., 1991, Proc. Natl. Acad. Sci. USA 88:5645–6549). Briefly, microtiter plates are coated with 5 ug/ml peptide-BSA conjugate, saturated with 2% BSA in phosphate-buffered saline(PBS) and incubated with various dilution of serum. Bound antibodies are revealed by using $^{125}$I labelled antimouse kappa monoclonal antibody.

Radioimmunoprecipitation

The H9 human T cell line is acutely infected with HIV. Four days postinfection, $5\times10^7$ infected cells are labelled with $^{35}$S-cysteine, $^{35}$S-methionine, and $^3$H-isoleucine at $2\times10^6$/ml in media containing 100 $\mu$Ci of each isotope per ml. After 20 h of metabolic labelling, the radioactive virions are pelleted by centrifugation for 1 h at 45,000 rpm. The pellet is then resuspended in 1.0 ml of lysis buffer containing 1% Triton X-100 and 2 mM phenylmethylsulfonyl fluoride (PMSF). Approximately 20 $\mu$l of sera or 0.5 $\mu$g of monoclonal antibody (in 20 $\mu$l PBS) and 175 $\mu$l of virion lysate are incubated overnight at 4° C. in 0.5 ml immunoprecipitation buffer containing 0.5% sodium dodecyl sulfate (SDS), 1 mg/ml BSA, 2% Triton X-100, and 50 mM sodium phosphate (pH 7.4). The antigen-antibody complexes are bound to protein A-Sepharose beads, and are analyzed by electrophoresis on a 10% SDS-polyacrylamide gel.

HIV-1 Neutralization Assays

The in vitro neutralization assay are performed as described previously (Nara, P. L. et al., 1987, AIDS Res. Hum. Retroviruses 3:283–302). Briefly, serial twofold dilutions of heat-inactivated serum are incubated for 1 h at room temperature with 150–200 syncytium forming units of HIV virus produced in H9 cells. The virus/serum mixture is incubated for 1 h at 37° C. with 50,000 DEAE-dextran treated CEMss cells (adhered to microplate dishes using poly-L-lysine), or 50,000 H9 suspension cells. After virus adsorption, the unbound virus is removed and 200 $\mu$l of media is added to each well. Four days postinfection, 50 $\mu$l of supernatant media is removed for viral $p24^{gag}$ protein quantitation (Coulter Source, Inc.). The total number of syncytia in CEMss cells is counted five days postinfection. The neutralization titers are calculated by comparison with control wells of virus only, and are expressed as the reciprocal of the highest serum dilution which reduced syncytia numbers by more than 50% or inhibited the p24 synthesis by more than 50%.

Induction of CTL Response

BALB/c mice is immunized with 0.2 ml viral suspension containing $10^7$ PFU of chimeric NDV virus. 7 days later, spleen cells are obtained and restimulated in vitro for 5 days with irradiated spleen cells, alone or coated with immunogenic peptides, in the presence of 10% concanavalin A in the supernatant as previously described (Zaghouani, H. et al., 1992, J. Immunol. 148:3604–3609).

Cytolysis Assay

The target cells coated with peptides are labeled with $Na^{51}Cr_4$ (100 $\mu$Ci/$10^6$ cells) for 1 h at 37° C. After being washed twice, the cells are transferred to V-bottom 96-well plates, the effector cells are added, and incubated at 37° C. in 7% $CO_2$. Four hours later, the supernatant is harvested and counted. The maximum chromium release is determined by incubating the cells with 1% Nonidet P40 detergent. The percentage of specific lysis is calculated according to the following formula: [(cpm samples−cpm spontaneous release)/(cpm maximum release−cpm spontaneous release)]×100.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All references cited herein are incorporated herein by reference in the entirety for all purposes.

What is claimed is:

1. A recombinant RNA molecule comprising a binding site specific for an RNA-directed RNA polymerase of a Newcastle disease virus, operatively linked to a viral RNA containing a heterologous RNA sequence.

2. A recombinant RNA molecule comprising a binding site for an RNA-directed RNA polymerase of a Newcastle disease virus operatively linked to a Newcastle disease viral gene containing a mutation, which mutation results in an attenuating phenotype.

3. The recombinant RNA molecule of claim 1 or 2 in which the polymerase binding site comprises the polymerase binding site contained in the 3'-noncoding flanking region of a Newcastle disease viral RNA genome.

4. The recombinant RNA molecule of claim 3 in which the 3'-noncoding flanking region has a viral sense sequence as shown in FIG. 1.

5. The recombinant RNA molecule of claim 1 in which the heterologous RNA encodes an antigen or an epitope from human immunodeficiency virus-1 or human immunodeficiency virus-2.

6. The recombinant RNA molecule of claim 1 in which the heterologous RNA encodes an antigen or an epitope from the env gene of human immunodeficiency virus-1 or human immunodeficiency virus-2.

7. A recombinant cell comprising nucleotide sequences encoding a recombinant NDV molecule of claim 1 and an NDV RNA polymerase protein.

8. A chimeric virus comprising a negative strand RNA virus containing a viral RNA containing a heterologous RNA sequence comprising the reverse complement of a coding sequence derived from the genome of a Newcastle disease virus, operatively linked to a polymerase binding site of the negative strand RNA virus.

9. The chimeric virus of claim 8 in which the heterologous RNA encodes an antigen or an epitope from human immunodeficiency virus-1 or human immunodeficiency virus-2.

10. The chimeric virus of claim 8 in which the heterologous RNA encodes an antigen or an epitope from the env gene of human immunodeficiency virus-1 or human immunodeficiency virus-2.

11. The chimeric virus of claim 8 in which the heterologous RNA is contained within the HN gene of Newcastle disease virus.

12. A method for producing a chimeric negative-strand RNA virus, comprising transfecting a host cell with nucleotide sequences encoding recombinant NDV and recovering the chimeric virus from the culture.

13. The method of claim 12 in which the recombinant NDV comprises nucleotides encoding an antigen or an epitope from human immunodeficiency virus-1 or human immunodeficiency virus-2.

14. The method of claim 12 in which the recombinant NDV comprises nucleotides encoding an antigen or an epitope from the env gene of human immunodeficiency virus-1 or human immunodeficiency virus-2.

* * * * *

SEQUENCE LISTING

<160> NUMBER OF SEQ ID NOS: 4

<210> SEQ ID NO 1
<211> LENGTH: 121
<212> TYPE: RNA
<213> ORGANISM: Newcastle Disease Virus

<400> SEQUENCE: 1
accaaacaga gaauccguaa gguacguuaa aaagcgaagg agcaauugaa gucgcacggg      60
uagaaggugu gaaucucgag ugcgagcccg aagcacaaac ucgagaaagc cuucuaccaa     120
c                                                                    121

<210> SEQ ID NO 2
<211> LENGTH: 196
<212> TYPE: RNA
<213> ORGANISM: Newcastle Disease Virus

<400> SEQUENCE: 2
cuuaacgaca aucacauauu aauaggcucc uuuucuggcc aauuguaucc uuguugauuu      60
aaucauacua uguuagaaaa aaguugaacu ccgacuccuu aggacucgaa cucgaacuca     120
aauaaauguc uuagaaaaag auugcgcaca guuauucuug aguguagucu ugucauucac     180
caaaucuuug uuuggu                                                    196

<210> SEQ ID NO 3
<211> LENGTH: 64
<212> TYPE: DNA
<213> ORGANISM: Newcastle Disease Virus

<400> SEQUENCE: 3
tggtttgtct cttaggcatt ccatgcaatt tttcgcttcc tcgttaactt catgcccatc      60
ttcc                                                                  64

<210> SEQ ID NO 4
<211> LENGTH: 67
<212> TYPE: DNA
<213> ORGANISM: Parainfluenza Virus

<400> SEQUENCE: 4
tggtttgtct cttaggcatt ccatgctatt ttccgcttcc tcgttaactt cagcatgccc      60
atcttcc                                                               67